United States Patent [19]

Chan et al.

[11] 4,006,196
[45] Feb. 1, 1977

[54] PROCESS FOR THE MANUFACTURE OF GERANYL CHLORIDE

[75] Inventors: Jimmy H. Chan, Martinez; Harold M. Pitt, Lafayette, both of Calif.

[73] Assignee: Stauffer Chemical Company, Westport, Conn.

[22] Filed: Mar. 4, 1976

[21] Appl. No.: 663,948

[52] U.S. Cl. .................... 260/654 R; 260/564 R
[51] Int. Cl.$^2$ ............................... C07C 21/00
[58] Field of Search ............... 260/654 R, 564 R

[56] References Cited

FOREIGN PATENTS OR APPLICATIONS 987,520   3/1965   United Kingdom ........... 260/654 R Primary Examiner—Delbert E. Gantz
Assistant Examiner—Joseph A. Boska
Attorney, Agent, or Firm—Joel G. Ackerman; Daniel C. Block

[57] ABSTRACT

A novel process for the manufacture of geranyl chloride, a useful intermediate in the manufacture of compounds useful in controlling insects, which comprises reacting geraniol and chlorodimethylformiminium chloride to produce the desired product.

8 Claims, No Drawings

PROCESS FOR THE MANUFACTURE OF GERANYL CHLORIDE

SUMMARY OF THE INVENTION

This invention relates to a novel process for the manufacture of geranyl chloride, also known by its synonym, 8-chloro-2, 6-dimethyl-2,6-octadiene. This compound is useful as an intermediate in the manufacture of the epoxides of certain geranylphenyl ethers which are known for their usefulness in controlling insects by exerting a disrupting influence upon the normal development of the insects. A description of these epoxides of geranylphenyl ethers and the use of geranyl chloride in their manufacture is found in U.S. Pat. No. 3,825,602. The present invention relates to a process for the manufacture of geranyl chloride which is both economical and results in a product of a high degree of purity.

BACKGROUND OF THE INVENTION

A wide variety of processes are known in the art for the preparation of geranyl chloride. The compound can be prepared from myrcene by hydrohalogenation in the presence of a Cu catalyst (U.S. Pat. Nos. 3,016,408 and 2,871,271). It can also be prepared from linalool by reaction with $SOCl_2$, $PCl_3$, $PCl_5$, $COCl_2$, or HCl. Geraniol has also been used extensively as the starting material, most notably by treatment with $PCl_3$ or $PCl_5$ [L. Ruzicka, Helvetica Chim. Acta 6, 483–92 (1923)], and by treatment with a mixture of methanesulfonyl chloride, lithium chloride and dimethylformaide [E. W. Collington and A. I. Meyers, J. Org. Chem 36 (20), 3044 (1971)].

Many of the above reactions give extensive rearrangement products including elimination products. Others are costly and impractical as commercial processes.

The process of the present invention provides the advantage of favorable process economics, and produces the desired product in very high purity and yields.

DESCRIPTION OF THE INVENTION

In the practice of the present invention, geraniol, also known by the synonym 2,6-dimethyl-2,6-octadiene-8-ol is reacted with chlorodimethylformiminium chloride to produce geranyl chloride.

The invention relates to the above reaction regardless of the methods of preparation of the starting materials. An example of the preparation of chlorodimethylformiminium chloride is the reaction between N,N-dimethylformamide with phosgene gas. Since the latter reaction also produces gaseous HCl, its efficiency and stoichiometry will be enchanced if the rate of addition of the gaseous phosgene is slow enough to prevent the HCl produced from sweeping out of the reaction mixture any substantial amount of the phosgene. The chlorodimethylformiminium chloride reaction preferably occurs in the presence of a non-reactive solvent, for example benzene, toluene, chloroform, methylene chloride, ethylene dichloride, carbon tetrachloride, hexane, pentane, etc. The use of a solvent will serve to moderate the reaction and to shield the resultant product from exposure to air, thus preventing the reaction between chlorodimethylformiminium chloride and the moisture in the air. Exposure to moisture can also be prevented by running the chlorodimethylformiminium chloride reaction in an atmosphere of ivert dry gas, e.g., nitrogen or dry air.

The process of the invention, the reaction between geraniol and chlorodimethylformiminium chloride, can also be conducted in the presence of a nonreactive solvent which will serve the function, among others, of moderating the reaction. When the reactions to form chlorodimethylformiminium chloride and geranyl chloride are performed in succession, it will be convenient to use the same solvent for both reactions.

In reactions performed subsequent to the process of the invention, for instance, whereby geranyl chloride is further reacted to form an epoxide as mentioned in the Summary of the Invention above, the same solvent can again be used. The yield of the epoxide can be improved, however, by removal of any light ends formed in the geranyl chloride reaction prior to the formation of the epoxide. Further purification can be done either before or after the epoxide reaction or any other reaction performed subsequent to the formation of geranyl chloride.

The particular temperature and pressure at which the reaction to form geranyl chloride is performed are not essential to the process of the invention. The reaction temperature is primarily limited by the melting and boiling points of the solvent used; it is generally convenient to run the reaction at a temperature between about 0° and about 80° C, with about 20° to about 40° C preferred. Likewise, it will be convenient to use a pressure ranging from about 0.8 to about 4.0 atmospheres.

The reaction can be conducted with approximately equimolar amounts of geraniol and chlorodimethylformiminium chloride. An excess of either of the reactants can also be used. In particular, an excess of the chlorodimethylformiminium chloride will provide the advantage of complete removal of geraniol from the system. This will be a desirable result when the geranyl chloride thus formed is further reacted to form the epoxide and subsequently the phenyl ether as described in U.S. Pat. No. 3,825,602.

When a solvent is used, the reaction mixture will form two liquid phases, with the desired product, geranyl chloride, residing in the upper phase. These phases can be separated by decantation or any other conventional separation technique, and, if desired, the product can be recovered from the upper phase and purified, by conventional purification procedures, such as evaporation or distillation. When no solvent is used, the geranyl chloride will itself form an upper phase which can be separated and purified in the same manner as indicated above.

Optionally, a quenching reagent can be added to either or both phases at any point in time after the reaction. When the above-described chlorodimethylformiminium chloride reaction is used, a quenching reagent can also be used after such reaction. The reagent in either case will be a weak base, for example a 10% sodium carbonate solution or a 5% sodium hydroxide solution. The base will serve to neutralize any acidic species remaining in solution and thus improve the stability of the desired product.

The following example is offered to further illustrate the process of the invention.

EXAMPLE

Into a 2-liter round bottom flask was placed 176 g (2.40 moles) anhydrous dimethylformamide (DMF)

and 800 ml dry benzene. Phosgene gas (210 g, 2.10 moles) was bubbled into the solution over a period of 8 hours. As the reaction progressed, chlorodimethylformiminium chloride precipitated as a white solid. The reaction was mildly exothermic and the temperature of the reaction rose from 24° to 36° C. When the phosgene addition was complete, anhydrous granular sodium carbonate (5.3 g, 0.05 mole) was added to the solution.

Next, 310 g (2.0 moles) geraniol (92% pure) was added over a period of 35–40 minutes and the reaction was moderated by an ice-water bath. The solid dissolved and a clear light yellow-brown solution resulted. The solution was stirred for several hours. The resulting mixture was analyzed by vapor phase chromatography, which showed about 3 area percent unreacted geraniol. An additional 8 g of phosgene served to eliminate any detectable amounts of geraniol in the reaction mixture.

The reaction mixture formed two liquid phases, the lower of which, containing DMF, chlorodimethylformiminium chloride and sodium carbonate, was drawn off and discarded. The upper phase was washed with aqueous 10% sodium carbonate solution and subsequently with water. The solvent was then evaporated from the mixture to give a product of the following analysis in area percent by vapor phase chromatography

| | |
|---|---|
| Light ends | 2.7% |
| Linalyl chloride | 8.4% |
| Neryl chloride | 9.7% |
| Geranyl chloride | 73.2% |
| Heavy ends | 3.7% |
| Geranyl dichloride | 2.0% |

The weight of geranyl chloride was 342 g (98% technical yield).

What is claimed is:
1. A process for the manufacture of geranyl chloride comprising reacting geraniol and chlorodimethylformiminium chloride.
2. The process of claim 1 in which the reaction occurs at a temperature between about 0° and about 80° C.
3. The process of claim 1 in which the reaction occurs at a temperature between about 20° and about 40° C.
4. The process of claim 1 in which the reaction occurs at a pressure between about 0.8 and about 4.0 atmospheres.
5. The process of claim 1 in which the reaction occurs in the presence of a nonreactive solvent.
6. The process of claim 1 in which the chlorodimethylformiminium chloride is obtained by reaction of N,N-dimethylformamide with phosgene.
7. The process of claim 6 in which the reaction to form chlorodimethylformiminium chloride occurs in the presence of a nonreactive solvent.
8. The process of claim 1 further comprising recovering geranyl chloride from the reaction mixture.

* * * * *